(12) United States Patent
da Luz Moreira et al.

(10) Patent No.: US 8,652,536 B2
(45) Date of Patent: Feb. 18, 2014

(54) SKIN CLARIFYING COMPLEX, USE OF SAID COMPLEX, COSMESTIC OR PHARMACEUTICAL COMPOSITION COMPRISING SAID COMPLEX AND METHOD FOR APPLICATION THEREOF

(75) Inventors: Patricia da Luz Moreira, Bairro Vila Romana (BR); Cintia Rosa Ferrari, Carapicuiba (BR); Rosa Maria Teixeira Tage Biaggio, São José dos Campos (BR); Adriano Tadeu Siqueira Jorge, Agua Rasa (BR); Kelen Fabiola Arroteia, Campinas (BR)

(73) Assignee: Natura Cosmeticos S.A., Itapecerica da Serra SP (BR)

( * ) Notice: Subject to any disclaimer, the term of this patent is extended or adjusted under 35 U.S.C. 154(b) by 0 days.

(21) Appl. No.: 13/389,550

(22) PCT Filed: Aug. 17, 2010

(86) PCT No.: PCT/BR2010/000268
§ 371 (c)(1),
(2), (4) Date: Apr. 16, 2012

(87) PCT Pub. No.: WO2011/020167
PCT Pub. Date: Feb. 24, 2011

(65) Prior Publication Data
US 2012/0189565 A1 Jul. 26, 2012

(30) Foreign Application Priority Data

Aug. 17, 2009 (FR) ..................... 09 55693

(51) Int. Cl.
*A61K 36/00* (2006.01)
*A61K 31/375* (2006.01)
(52) U.S. Cl.
USPC .......................................... 424/725; 514/474
(58) Field of Classification Search
None
See application file for complete search history.

(56) References Cited

U.S. PATENT DOCUMENTS

| 5,078,989 A | 1/1992 | Ando et al. |
| 5,656,278 A * | 8/1997 | Enjolras ........................ 424/401 |
| 2008/0253982 A1* | 10/2008 | Shibayama et al. ............ 424/62 |

FOREIGN PATENT DOCUMENTS

| JP | 2005-272444 | 10/2005 |
| JP | 2005-272471 | 10/2005 |
| JP | 2005336113 A * | 12/2005 |
| WO | WO 01/08652 A1 * | 2/2001 |

OTHER PUBLICATIONS

Cavalher-Machado et al, The anti-allergic activity of the acetate fraction of *Schinus terebinthifolius* leaves in IgE induced mice paw edema and pleurisy. International immunopharmacology, (Nov. 2008) vol. 8, No. 11, pp. 1552-1560.*
International Search Report and Written Opinion for International Application No. PCT/BR2010/000268, mailed Dec. 7, 2010.
Cavalher-Machado, S.C., et al.; "The anti-allergic activity of the acetate fraction of *Schinus terebinthifolius* leaves in IgE induced mice paw edema and pleurity"; International Immunopharmacology; vol. 8; Issue 11; Nov. 2008; pp. 1552-1560.
Database WPI; Week 200918; Thomson Scientific; London, GB; AN 2009-B48145; XP002575553 & KR 100 848 800 B1 (Bio Spectrum Inc.); Jul. 31, 2008; Abstract.

* cited by examiner

*Primary Examiner* — Quiwen Mi
(74) *Attorney, Agent, or Firm* — Alston & Bird LLP

(57) ABSTRACT

It is disclosed a skin clarifying complex comprising gallic acid and linoleic acid. It is further provided that the gallic acid can be obtained from *Shinus* sp and the linoleic acid can be obtained from passion flower oil. It is further disclosed the cosmetic or pharmaceutical use of the clarifying complex and a cosmetic or pharmaceutical composition comprising 0.25 to 10%, by weight, of said clarifying complex. The clarifying complex exhibits a high skin, spot and sprecke clarifying effect.

11 Claims, 3 Drawing Sheets

US 8,652,536 B2

SKIN CLARIFYING COMPLEX, USE OF SAID COMPLEX, COSMESTIC OR PHARMACEUTICAL COMPOSITION COMPRISING SAID COMPLEX AND METHOD FOR APPLICATION THEREOF

The present invention refers to a skin clarifying complex prepared by obtaining and combining gallic acid and linoleic acid. The present invention further refers to a cosmetic or pharmaceutical use of said complex for preparing cosmetic or pharmaceutical compositions, to cosmetic or pharmaceutical compositions comprising said complex and a method for applying this cosmetic or pharmaceutical composition containing said complex.

STATE OF THE ART

Melanin is produced by melanocytes which are cells from the basal layer of the epidermis which are in contact with keratinocytes via cytoplasmic projections. These extensions allow for the melanin pigments produced to be deposited onto keratinocytes.

The synthesis of melanin is basically mediated by the presence of an enzyme-tyrosinase-concentrated in the Golgi apparatus of melanocytes. This pigment comes from the polymerization of amino acid tyrosine via the action of tyrosinase, which turns from a colorless amino acid to a brownish pigment. The polymerized tyrosine is deposited on vesicles called melanosomes, which move across the melanocyte cytoplasmic projections, and suffer phagocytosis by keratinocytes, concentrating on the keratin layer.

The several layers of keratinocytes bearing melanin provide the underlying tissues an effective defense against the noxious effects from sunbeams, specially ultraviolet beams.

Cosmetic and pharmacological intervention with this melanin production cascade is known from the state of the art, aiming to provide local depigmentation or harmonize the skin hue. In this context, there is a great interest in using one or more components selected from plant phenolic compounds and lipid molecules for that purpose, for example, tannin and fatty acids.

US 2005/0163731 refers to a topical composition intended to depigmentating the skin comprising, in a physiologically acceptable medium, at least one depigmentating active ingredient in combination with an effective amount of adapalene acting as an depigmentation accelerant. The depigmentating agents consist of phenolic compounds, plant extracts and linoleic acid.

KR20030007990 refers to a cosmetic composition containing extract from *Houttuynia cordata, Gossypium indicum, Alpinia speciosa, Schum e Morus alba*; which promote anti-aging and whitening effects on the skin. These plant extracts are stabilized into a liquid crystal liposome comprising, in addition to other ingredients, ceramide, hydrogenated lecithin, sphingolipid derivatives and linoleic acid.

JP2005272471 describes a gallic acid and linoleic acid ester conjugate having a skin whitening—inhibition of tyrosinase—and anti-inflammatory (inhibition of COX-1 e COX-2) effect.

US 2006/0198800 relates to a cosmetic composition comprising an anti-wrinkles agent and natural exfoliating complex, the anti-wrinkle agent consisting of acetyl-hexapeptide. Moreover, that document describes the use, in preparing the compositions, of cosmetic adjuvants, such as, skin clarifying actives, wherein among the choices of clarifying agents there can be found gallic acid, phenolic compounds and several plant extracts.

Finally, PI 9916440-0 refers to a topical composition comprising linoleic acid conjugate and/or derivatives thereof, with 1% of the total components being represented by components in their 10-trans and 12-cis forms; in addition to a dermatologically acceptable vehicle. That document discloses a final product intended to clarifying human skin.

Thus, from the following description of the present invention, it may be concluded that it is not known in the state of art a clarifying complex comprised of gallic acid preferably obtained from Brazilian peppertree extract and linoleic acid preferably obtained from passion flower oil. Besides, a cosmetic or pharmaceutical composition comprising said complex, also an object of this invention, exhibits enhanced efficacy on skin depigmentation.

Objects of The Invention

It is an object of the present invention to provide a clarifying complex comprising gallic acid and linoleic acid.

It is also an object of the present invention to provide a cosmetic or pharmaceutical composition having enhanced efficacy on skin depigmentation, comprised of the above-mentioned clarifying complex.

Yet, it is a further object of the present invention to provide to provide the use of the clarifying complex in the manufacture of cosmetic or pharmaceutical compositions, in addition to a method of application of said cosmetic or pharmaceutical compositions to the skin.

BRIEF DESCRIPTION OF THE INVENTION

It is the object of the invention a skin clarifying complex comprising gallic acid and linoleic acid.

It is also an object of the present invention:
to obtain gallic acid from Brazilian peppertree
to obtain linoleic acid from passion flower oil
a cosmetic or pharmaceutical use the clarifying complex,
a method of application of the clarifying complex consisting of:
  (i) selecting an area of the body to be depigmentated; and
  (ii) applying to said area of the body the clarifying complex;
a cosmetic or pharmaceutical composition comprising:
  (i) said clarifying complex; and
  (ii) a physiologically acceptable vehicle.
a method of application of a cosmetic or pharmaceutical depigmentating composition consisting of: (i) selecting an area of the body to be depigmentated; and (ii) applying to said area of the body the cosmetic or pharmaceutical depigmentating composition comprising said clarifying complex.

BRIEF DESCRIPTION OF THE FIGURES

The present invention will now be described in more details based on a example shown in the drawings. The figures illustrate.

DETAILED DESCRIPTION OF THE INVENTION WITH

According to a preferred embodiment and as can be seen in FIGS. 1 to 6, the present invention refers to a clarifying complex, the cosmetic or pharmaceutical use of the clarifying complex, a cosmetic or pharmaceutical composition comprising certain concentrations of this complex and, further, a method of application of this complex and cosmetic and pharmaceutical compositions.

As defined herein a complex intends to mean one containing 2 combined actives that although already known as skin clarifiers but joined together for the first time with enhanced results.

Such combination exhibited sinergism reaching a very high clarifying power, optimizing skin clarification, reducing the amounts of actives when isolated. Such complex can thus be used for skin clarification, skin whitening, spot and freckle soothing, being more effective than the use of these extracts alone.

It can be concluded that this concerns a simpler answer than those known from prior art, there being a need to combine no more than two clarifying compounds or develop a new compound via chemical reactions.

Clarifying Complex

The clarifying complex, object of the present invention, comprises gallic acid and linoleic acid.

In preferred embodiments, the clarifying complex comprises from 0.025 mg/ml to 5 mg/ml, more preferably from 0.025 mg/ml to 0.075 mg/ml, of linoleic acid and from 0.025 mg/ml to 5 mg/ml gallic acid.

Preferably, the gallic acid is obtained from Brazilian peppertree extract also known as "aroeira" (*Schinus terenbinthifolius*).

Preferably, the linoleic acid is obtained from passion flower oil (*Passiflora alata*).

Thus, a preferred embodiment can also be a clarifying complex comprising 0.025 mg/ml to 5 mg/ml linoleic acid and 0.025 mg/ml to 5 mg/ml de Brazilian peppertree extract based on the total mass of the complex.

Gallic Acid

Gallic acid is a chemical compound already known is the state of the art as a skin clarifier.

Preferably, it is obtained from Brazilian peppertree or "aroeira". It can also be obtained from other sources.

In a preferred embodiment, *Schinus terenbinthifolius* extract is obtained via an aqueous extraction route, under steam pressure.

Figure 1:
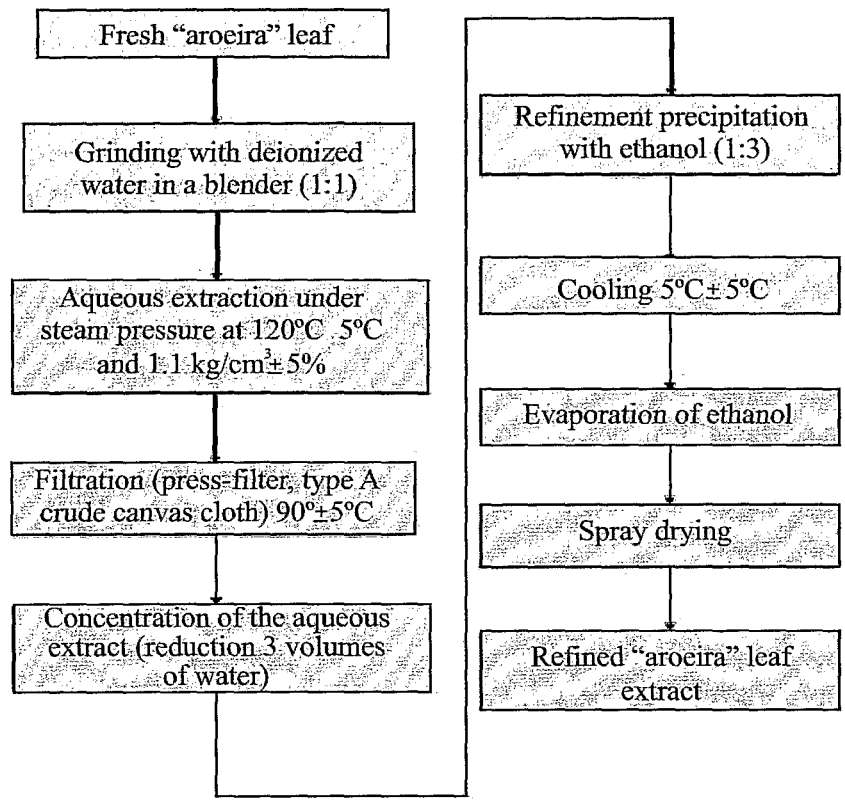
FIG. 1—is a flow chart showing details of the steps of a preferred technical route for obtaining Brazilian peppertree extract that is an object of the present invention.

As can be seen in the flow chart shown in FIG. 1, first fresh leaves of Brazilian peppertree ("aroeira") are selected and ground with water. Then a 7 fold aqueous extraction (this ratio consists is 1 part of plant to 7 parts of extracting solvent (water) under steam pressure at 85° C. to 110° C. and 1.60-2.4 Kgf/cm$^2$) is carried out. The resulting extracting solution is then filtered through a press-filter using a crude canvas filtering element, for example, at a temperature between 85° C. to 95° C. thus obtaining a filtrate and a supernatant.

The aqueous extract is concentrated under vacuum so as the amount of water is reduced by 3 volumes. Subsequent to this concentration step, refining/precipitation with alcohol (ethanol) takes place at a ratio of 1:3, followed by cooling to a filtrate temperature in the range from 0° C. to 10° C. and evaporation of alcohol (ethanol).

Finally, the filtrate is dried in a spray dryer, for example, resulting in a refined extract of *Schinus terenbinthifolius* leaves.

The refined extract is characterized in a quantitative gallic acid dosage assay by HPLC and a centesimal analysis shows the composition given in table 1 below, compared to the crude extract.

| Assays | Unit | crude extract (BA018) | refined extract (BA021) |
|---|---|---|---|
| gallic acid contents | % | 13.24 | 16.16 |
| total glycides | % | 15.76 | 14.32 |
| total tannins | % | 50.54 | 50.41 |
| ethereal extract | % | 0.13 | 0.08 |
| crude protein | % | 3.86 | 4.18 |
| mineral substance | % | | |

As can be seen in table 1 above, the refined extract exhibits higher contents (%) in total tannins, the biomarker for such extract being gallic acid, the main responsible for the depigmentating activity of the Brazilian peppertree extract as compared to the crude extract. Therefore, the process described in the present invention provides an optimum yield regarding the amount of gallic acid present in "aroeira", leading to the clarifying effect described hereinbelow.

Linoleic Acid

Linoleic acid is also known in skin clarification.

Linoleic acid present in this clarifying complex can be in its free or conjugated form, preferably used in its free form.

Figure 2:
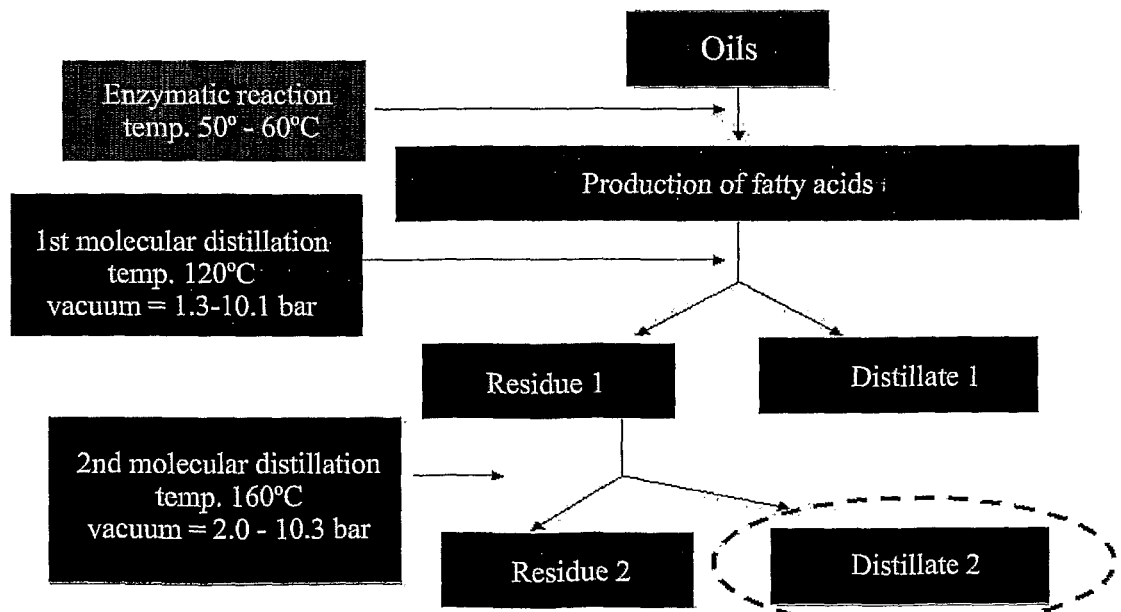
FIG. 2—is a flow chart showing details of the steps of a preferred technical route for obtaining do passion flower oil that is an object of the present invention.

As to the linoleic acid, this is obtained from vegetable oils, preferably from passion flower oil, more preferably via a route comprised of enzymatic hydrolysis and molecular distillation as shown in FIG. 2.

First, the vegetable oil (triglycerides and others) suffers an enzymatic reaction at a temperature from 50° C. to 60° C. in order to produce fatty acids. Thereafter, a first step of molecular distillation occur at a temperature of about 120° C. under a vacuum of 0.13 mBar. The residue and a first distillate are separated. This first distillate suffers a second step of molecular distillation at a temperature of about 160° C. and a vacuum of 0.002 mBar, thus obtaining a second residue and the final distillate in bulk yield of 61% and conversion rate of free fatty acids of 100%.

The enzymes used in this process are selected from:
Lipozyme TL 100l;
CALB; and
CALA.

The useful enzyme mixtures observe a ratio varying between 1:1 and 9:1 of Lipozyme TL 100L×CALB or CALA.

The mixture with enzymes Lipozyme TL 100l: CALA (1:1) showed the best results, with a conversion of 95.9%, which can be explained by a specificity of 1.3 for the enzyme Lipozyme TL 100l together with the best performance in hydrolysis by enzyme CALA, and the non-specificity thereof (hydrolysis in 2-position of the triglyceride chain).

Thus, it can be concluded that the object of the invention is the combination of those two actives unexpectedly potentiating skin clarification and heretofore unknown.

Optional Component

Yet, the present clarifying complex optionally contains ascorbic acid and/or derivatives thereof, at a ratio from 0.025 mg/ml to 15 mg/ml for serum concentrated formulations in the gel form. This embodiment can exhibits further enhanced efficacy.

Preferably, the process for stabilizing ascorbic acid is used in this invention, as described in Pl 9704418-0 and Pl 9704728-7 assigned to the same applicant of the present application.

Action of the Mixture According to the Present Invention

The mechanism of action of this clarifying complex is based on two main principles: 1) inhibition of tyrosinase and 2) degradation of tyrosinase. 1) Inhibition of Tyrosinase Hydrolisable tannins (gallic acid) present in high amounts in the *Schinus terenbinthifolius* extract inhibit the tyrosinase activity through the copper quelating property thereof, an essential co-factor for this enzyme activity, thus preventing it to act on melanin.

2) Degradation of Tyrosinase in the Medium

Linoleic acid acts on the tyrosinase present in the medium, accelerating the process of its degradation. Thus, a smaller amount of enzyme is available for the formation of melanin by melanocytes.

Figure 3:
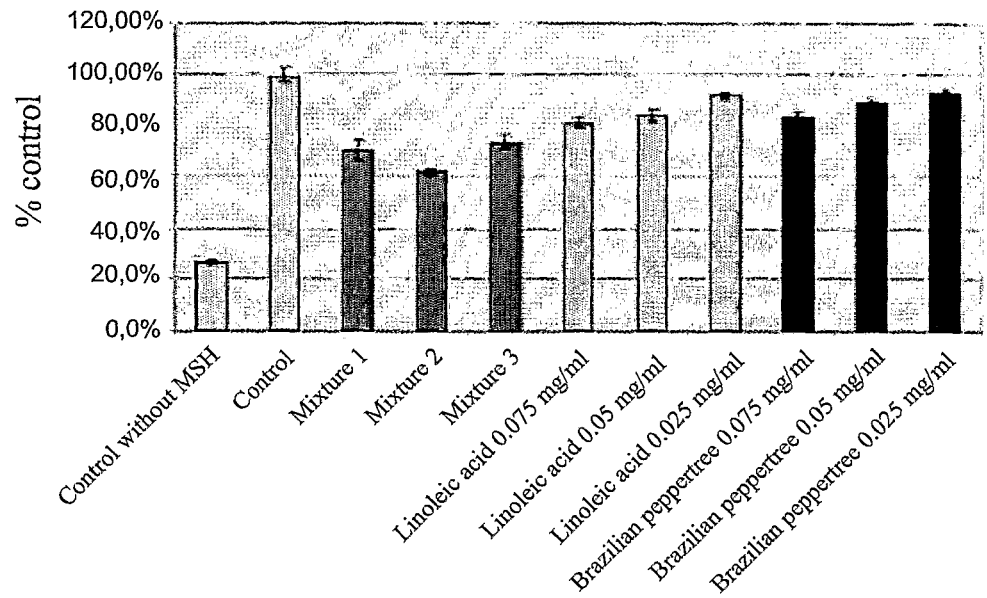
FIG. 3—is a graph illustrating the analysis of reduction in melanin synthesis performed by the clarifying complex that is the subject of the present invention.
Figure 4:
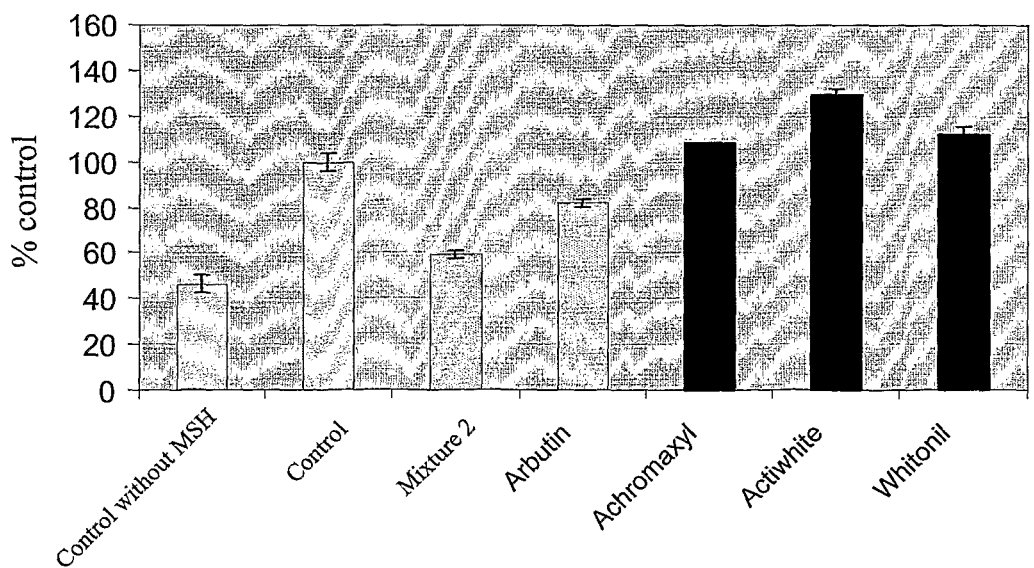
FIG. 4—is a graph illustrating the analysis of reduction in melanin synthesis performed by the clarifying complex compared to pharmaceutical actives.

FIGS. 3 and 4 illustrate the results from a test for assessing the activity of the clarifying complex of linoleic acid and *Schinus terenbinthifolius* extract according to this invention.

The assay methodology for the test lasted for five days in which, initially, line B16 melanocytes were plated on 12 well-conditioned containers, at a rate of 75,000 cells/plate.

On the three following days, 10mg (11 μl to linoleic acid) of component in the mixture were diluted in 100 μl of DMSO (dimethyl-sulfoxide) and, then, 9.9 ml of DMEM (culture medium) serum free were added so as to finally obtain 1 mg/ml of stock solution.

Sequentially, these solutions were incubated at 37° C. to assist solubilization of the samples. 10% bovine fetal serum (BFS) were added to the final dilution.

Table 2 below shows information on the composition of the mixtures used under the subject tests.

TABLE 2

| Mixture | Gallic acid | Linoleic acid | Total of active | Composition of the mixture |
|---|---|---|---|---|
| 1 | 0.05 mg/ml | 0.05 mg/ml | 0.1 mg/ml | 200 μL of stock solution of gallic acid + 200 μL of stock solution of linoleic acid + 8 μL de α-MSH to 500 μM + 3.592 ml of 10% SFB medium |
| 2 | 0.025 mg/ml | 0.075 mg/ml | 0.1 mg/ml | 100 μL of stock solution of gallic acid + 300 μL of stock solution of linoleic acid + 8 μL de α-MSH to 500 μM + 3.592 ml of 10% BFS medium |
| 3 | 0.075 mg/ml | 0.025 mg/ml | 0.1 mg/ml | 300 μL of stock solution of gallic acid + 100 μL of stock solution of linoleic acid + 8 μL of α-MSH to 500 μM + 3.592 ml of 10% BFS medium |

It shall be highlighted that α-MSH consists in melanocyte stimulating hormone acting on the production and release of melanin.

Table 3 below shows the concentration and composition of the solutions containing the actives alone. The actives are: gallic acid and linoleic acid.

TABLE 3

| Concentration | Composition |
|---|---|
| 0.075 mg/ml | 300 μl of stock solution + 8 μl de α-MSH to 500 μM + 3.692 ml of 10% FBS medium |
| 0.05 mg/ml | 200 μl of stock solution + 8 μl de α-MSH to 500 μM + 3.792 ml of 10% FBS medium |
| 0.025 mg/ml | 100 μl of stock solution + 8 μl de α-MSH to 500 μM + 3.892 ml of 10% FBS medium |

On day five of the test the cells were divided into two steps of characterization:

Assessment of melanin in which the cells were first "washed" with PBS and then the cellular layer was dissolved into 500 μl of 3N NaOH and the suspension homogenized by pipetting. Two 200 μl portions of suspension were plated for optical reading at 400 nm.

Table 4 shows the results of measurement of the amount of melanin detected after treatment of the cells with solutions of both linoleic acid and gallic acid only and table 5 shows the results of measurement of the amount of melanin detected after treatment of the cells with mixtures 1, 2 and 3 set forth in table 2 above.

TABLE 4

| | linoleic acid | | Brazilian peppertree | |
|---|---|---|---|---|
| Treatment | % control | Standard Deviation | % control | Standard Deviation |
| Control DMSO | 100.0% | 2.8% | 100.0% | 2.8% |
| 0.025 mg/ml | 91.9% | 0.9% | 92.5% | 2.2% |
| 0.05 mg/ml | 84.1% | 2.7% | 89.2% | 1.5% |
| 0.075 mg/ml | 81.0% | 2.1% | 83.4% | 2.2% |

TABLE 5

| | % control | Standard Deviation |
|---|---|---|
| Mixture 1 | 70.1% | 4.0% |
| Mixture 2 | 61.8% | 1.2% |
| Mixture 3 | 73.9% | 2.7% |

As illustrated in the graph in FIG. 3, the three mixtures (1, 2 and 3) exhibited enhanced reducing capacity of melanin synthesis as compared to the results obtained with treatment with solutions of each active alone.

Thus, it is concluded that the assessment of the whitening effect by melanin synthesis showed a specially interesting result for mixture 2 as identified in table 2, specially giving a result of 38.2% reduction in the amount of melanin as compared to the control assay.

Mixture 2 contains 0.025 mg/ml of gallic acid and 0.075 mg/ml of linoleic acid.

The synergistic effect of mixtures 1, 2 e 3 is evidenced from table 8 below. The three mixtures result in an additional inhibition when the effect obtained is compared to the effect expected.

TABLE 6

| | Linoleic acid alone | Gallic acid alone | Effect expected to additive effect | Synergistic effect obtained | Additional inhibition |
|---|---|---|---|---|---|
| Mixture 1 | 15.9% | 10.8% | 26.7% | 29.9% | 3.2% |
| Mixture 2 | 19% | 7.5% | 26.5% | 38.2% | 11.7% |
| Mixture 3 | 8.1% | 16.6% | 24.7% | 26.1% | 1.4% |

The tests above clearly show the unexpected synergistic effect obtained with the combination between gallic acid and linoleic acid, which exhibits excellent result in skin clarifying.

Mixture 2 having 0.025 mg/ml gallic acid and 0.075 mg/ml linoleic acid, amounting 0.01 mg/ml actives, exhibited better efficacy than Arbutin (a component in the pharmaceutical industry for the principle of clarification), when tested at the same concentration. This result is shown is FIG. 4. Further, mixture 2 exhibited better efficacy than the actives available in the market used at 0.01 mg/ml. It is important to stress that hydroquinone at the same concentration has caused significant death cell, showing that mixture 2 is less cytotoxic than the most common used pharmaceutical active for clarifying effect.

TABLE 7

| | % control | Standard deviation |
|---|---|---|
| Control without MSH | 46.5 | 4 |
| Control | 100 | 4 |
| Mixture 2 | 59.1 | 1.7 |
| Arbutin | 82.5 | 1.8 |
| Achromaxyl (ISP) | 108.2 | 0.6 |
| Actiwhite (Cognis) | 129.6 | 2.4 |
| Whitonil (Silab) | 112.1 | 3.2 |

Figure 5:
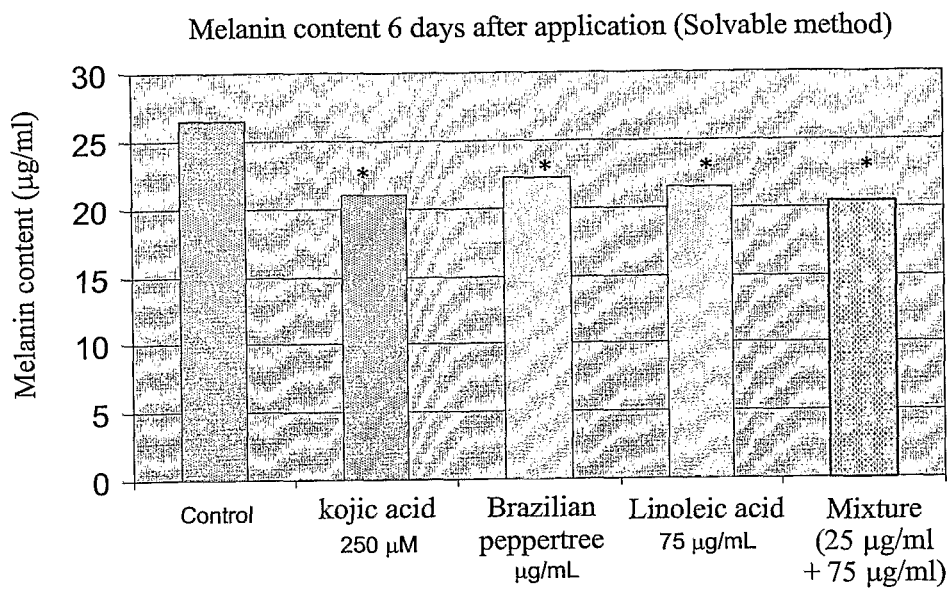
FIGS. 5 and 6—are graphs showing the analysis of reduction in melanin concentrations performed by the clarifying complex compared to the individual components and to kojic acid.
Figure 6:
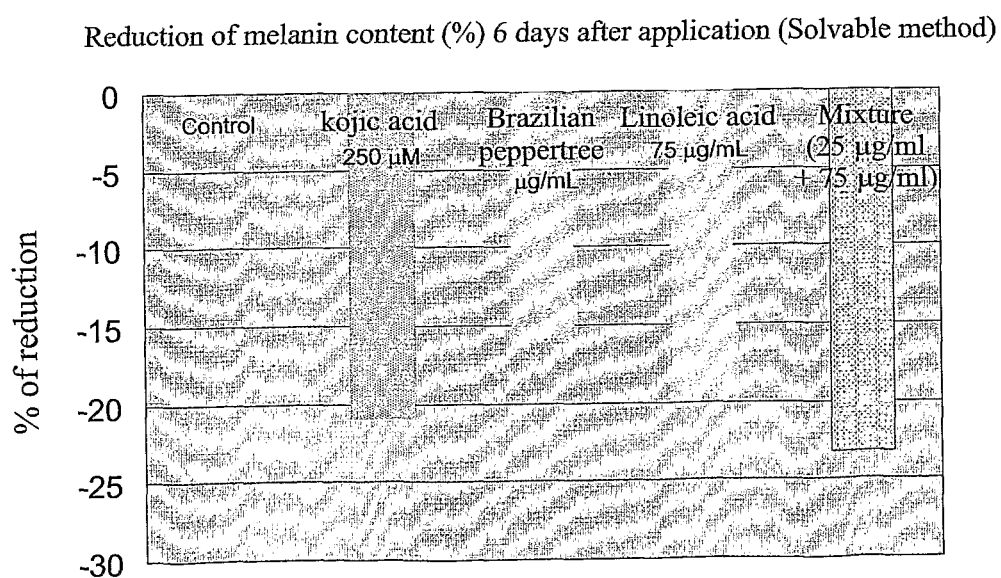

In another example samples containing an extract of Brazilian peppertree extract (A), linoleic acid (B) and a mixture of the active ingredients linoleic acid and gallic acid (A+B), respectively, were compared to a control and to kojic acid as far as the reduction of the amount of melanin is concerned. Each sample was applied to a culture medium corresponding to the epidermis and the concentrations of melanin were measured after 6 days of treatment. The results are shown in FIGS. 5 and 6 and Table 8.

TABLE 8

Percentage of reduction of melanin extracted from epidermis after a 6 days treatment

| | Mean (ug/mL) | Mean (%) | Reduction (%) |
|---|---|---|---|
| Control | 26.52564103 | 100 | 0 |
| Kojic acid 250 μM | 20.94871795 | 78.97535041 | 21.02464959 |
| A—25 μg/ml | 22.29487179 | 84.05026583 | 15.94973417 |
| B—75 μg/ml | 21.3974359 | 80.66698888 | 19.33301112 |
| A + B, 25 + 75 μg/ml | 20.37179487 | 76.80038666 | 23.19961334 |

The melanin reductions were comparable to the control (kojic acid 250 μM), the mixture A+B showing higher reduction than said control. As shown in Table 8 the reduction obtained with kojic acid was of about 21.02%, the reduction for Sample A was of 15.9%, for sample B was of 19.3% while the complex mixture A+B obtained a reduction of 23.19%.

In Vitro Safety Test:

Cytotoxicity assay allows determining the cytotoxic concentration of an active, when 3T3 cells are incubated therewith for 24 hours. Toxicity is determined as a function of cell viability, monitored by incubation of 3T3 cells with Neutral Red, and essential dye incorporated by living cells 24 hours 24 hours after contacting the active. Such assessment uses methodologies established by the National Institute of Health (NIH), USA, acknowledged internationally (Guidance NIH, 2001). The phototoxicity test is based on a comparison of the toxicity of an active in the presence and absence of a non-cytotoxic dose of UVA radiation. Phototoxicity is measured by Neutral Red capture by those cells surviving incubation with the active, according to a protocol already established and standardized by COLIPA and OECD (ZEBET/ECVAM/COLIPA, 1998; OECD, 2004). Phototoxicity/photoirritation is defined as the toxic response caused after a first exposure of the skin to certain products/actives and the subsequent exposure to sun light or induced by an irradiation of the skin after systemic administration of an active/product.

The following table 9 shows the results of cytotoxicity and phototoxicity tests carried out with *Schinus terenbinthifolius* extract and linoleic acid.

TABLE 9

| | Cytotoxicity | Phototoxicity |
|---|---|---|
| Gallic acid from *Schinus terenbinthifolius* extract | Not cytotoxic | Not phototoxic |
| Linoleic acid from passion flower oil | Not cytotoxic | Not phototoxic |

Cosmetic or Pharmaceutical Use of the Clarifying Complex

The cosmetic or pharmaceutical use of the clarifying complex already detailed above is intended to the manufacture of cosmetic or pharmaceutical compositions which are indicated to whiten or harmonizing the tone of keratinic material such as, for example, the skin.

Cosmetic or Pharmaceutical Composition

The cosmetic or pharmaceutical composition of the present invention comprises:

(i) from 0.25% to 10%, by weight, of the clarifying complex of the present invention; and (ii) a physiologically acceptable vehicle;

all amounts bases on the total mass of the composition.

Preferably, such composition comprises from 0.25% to 10% of a clarifying complex comprised of gallic acid and linoleic acid. More preferable is 1 part of gallic acid to 2 parts of linoleic acid in a physiologically acceptable vehicle.

Optionally the clarifying complex contained in this composition may comprise from 0.025 to 15 mg/ml ascorbic acid and/or derivatives thereof.

The main examples of gallenic forms of products which can be prepared from the clarifying complex herein or from cosmetic and pharmaceutical compositions comprising said clarifying complex are:

a) Fluid or semi-solid emulsion, such as, for example;
Body hydrating milk;
Facial hydrating milk;
Body hydrating lotion;
Facial hydrating lotion;
Sun protectors or blockers for adult and pediatric use, either intended to concomitant use with sports practicing or not;
Body or facial hydrating products;
Body or facial anti-age products;
Body or facial astringent products;
Facial or body clarifying, uniformizing and tanning products;
Insect repellents;
Body or facial skin lightening hydrating products;

Anti-cellulite products;
Products for sensitive skin;
Deodorants to antiperspirants (having a clarifying or uniformizing action on skin tone)
b) Gels, such as, for example:
Pharmaceutical preparations for topical application;
Body or facial cosmetic preparations for pediatric use;
Anti-acne products;
Anti-age products;
Anti-cellulite products;
Products for sensitive skin;
Exfoliating products;
Facial or body skin clarifying and/or uniformizing products;
c) Body cleanser products, such as, for example:
Liquid and bar soap cleansers;
Exfoliating products;
d) Suspensions, such as, for example:
Ointments;
Cosmetic preparations for local use, specific to the periocular region, lip contour, lips, anti-spots, anti-dark circles, and the like;
Liniments;
e) Powders, such as, for example:
Facial powders;
Body powders;
Make-ups;
f) Further examples:
Toners.

Concerning the physiologically acceptable vehicle, this consists of a usual cosmetic or pharmaceutical base according to intended use of the composition to be prepared. Such vehicle is composed of usual physiologically inert compounds and adjuvants.

The following is an illustrating but not limited list of some examples of adjuvants and inert constituents compatible with the composition properties described herein and which can be additionally employed in the present cosmetic and/or pharmaceutical composition intended to depigmentation of keratinic material:

- Water: Water is the base for numerous preferred embodiments of the cosmetic composition of the present invention, serving as a vehicle for the rest of the components. The compositions of the present invention comprise preferably demineralized or distilled water at a suitable percentage (q.s.p.) to 100% formula based on the total weight of the present composition. Obviously, other cosmetically acceptable vehicles can be used in the present invention.
- Anti-oxidant agents: BHT, BHA, tocopherol and/or derivatives thereof, catechins, tannins and/or derivatives thereof, phenolic compounds, and the like;
- Preservative agents: methyl parabens, propyl parabens, isothiazolinone derivatives, phenoxyethanol;
- Film-forming agents: agar gum, carrageenin gum, alginates, gum arabic, gelatin;
- Chelating agents: EDTA, citric acid, etidronic acid.
- Supporting microcrystalline network-forming agents: dextrans, methyl-acrylates, PHB, PHA;
- Polymeric agents and/or copolymeric agents: silicone copolymers, siloxane and/or modified silicone polymers, acrylate copolymers;
- Denaturating agents: denatonium benzoate;
- Bulking agents: vegetable waxes, mineral hydrocarbons, paraffin, beeswax, white paraffin, spermaceti, cocoa butter, shea butter, sugar cane wax;
- Emollients: liquid paraffin, palm oil, *Theobrama grandiflorum* butter, lecithin, milk amino acids, wheat protein, vegetable proteins, vegetable oils, phospholipids, keramides, passion flower keramide, sphingolipids, lanoline, almond oil, dicapryl carbonate, silicone elastomers, cyclomethicone;
- Humectating agents and/or hydrating agents: glycerine, propylene glycol, hialuronic acid, urea, PCA;
- Conditioning agents: quaternary ammonium salts, silicones, siloxanes;
- Further cosmetic actives, such as, for example, vegetable extracts, polysaccharides, serving the purpose of skin-aging treatment; and
- protecting agents against UV radiation glycerin (sun filters): octyl methoxycinnamate, benzophenones, etc.

The clarifying complex of the present invention, incorporated into cosmetic or pharmaceutical compositions as well as said composition shows a wide range of advantages and characteristics which are desired in a cosmetic or pharmaceutical skin product, some of which are described hereinbelow:

1. It is stable for an at least two year period;
2. It shows suitable texture during application, it is non-sticky and not oily;
3. It spreads easily;
4. It does not cause the skin to become oily after it is applied;
5. It does not show comedogenicity;
6. It does not show phototoxicity and cytotoxicity;
7. It does not show allergenicity;
8. It does not cause cutaneous or ocular adverse reactions or damage of any kind of, either under regular conditions of use or under forced sudoresis;
9. It has excellent homogeneity and stability;
10. Since it does not cause irritation to the skin, it is more comfortable and its use is allowed on a daily basis or even more than once a day;
11. It is suitably chemically stable;
12. The clarifying complex is not unpleasantly colored or scented so as not to change the desired organoleptic characteristics of the present composition;
13. The clarifying complex exhibits a high clarifying effect, being effective to skin clarification, skin whitening, spot and freckle soothing and even elimination of spots and freckles.

Example of a Cosmetic or Pharmaceutical Composition Comprising the Present Clarifying Complex

EXAMPLE 1

Emulsion

Component, % Application
DEMINERALIZED WATER 96.4480
BHT 0.5000
DISODIUM EDTA 0.1000
SODIUM BENZOATE 0.1000
BRAZILIAN PEPPERTREE EXTRACT 0.2500
DRY COCOA EXTRACT 0.0010
DRIED REFINED GREEN TEA EXTRACT 0.0010
SODIUM ACRYLIC ACID HOMOPOLYMER 0.1500
XANTHAN GUM C1911 B 1.5000
LINOLEIC ACID FROM PASSION FLOWER OIL 0.7500
TOCOPHERYL ACETATE (VITAMIN E)

EXAMPLE 2

Emulsion

Component, % Application
DEMINERALIZED WATER q.s. 100

LINOLEIC ACID FROM PASSION FLOWER OIL 0.2-3.0%
PROPYLENE GLYCOL 10.0-30.0%
XANTHAN GUM C1911 B 0.3-3.5%
SODIUM HYDROXIDE 0.01-0.3%
SODIUM BENZOATE 0.1-0.5%
BRAZILIAN PEPPERTREE EXTRACT 0.05-0.6
SODIUM ACRYLIC ACID HOMOPOLYMER—0.02-0.4
GLUTATIONE 0.03-0.35%
ETIDRONIC ACID 0.02-0.42%

EXAMPLE 3

Deodorant

Component, % Application
DEMINERALIZED WATER 54.17
DISODIUM EDTA 0.1000
PPG-15 STEARILIC ETHER 1.0000
CICLOMETHICONE D5/D6 VS7158 2.5000
ALUMINIUM SESQUICHLOROHYDRATE 40.0000
IODOPROPINYL BUTYLCARBAMATE 0.1800
DMDM HYDANTOIN-IPBC 0.05
LINOLEIC ACID FROM PASSION FLOWER OIL 0.7500
BRAZILIAN PEPPERTREE EXTRACT 0.2500

Method of Applying the Clarifying Complex or Cosmetic or Pharmaceutical Composition Comprising a Clarifying Complex The method of applying the clarifying essentially consists in selecting an area of the body to be depigmentated and applying the clarifying complex comprising gallic acid and linoleic acid to said area of the body.

This mixture applied as such or as a composition may further comprise from 0.05 to 15 mg/ml ascorbic acid or derivatives thereof.

Having described an example of a preferred embodiment, it is to be understand that the scope of the present invention embraces other possible variations, only limited by the appended claims below, possible equivalents included therein.

The invention claimed is:

1. A skin clarifying complex, comprising:
    (i) gallic acid present at a concentration varying from 0.025 mg/ml to 5 mg/ml; and
    (ii) linoleic acid present at a concentration varying from 0.025mg/ml to 0.075 mg/ml.

2. The complex as claimed in claim 1, characterized in that the gallic acid is obtained from *Schinus terebinthifolius* extract.

3. The complex as claimed in claim 2, characterized in that it comprises from 0.025 mg/ml to 5 mg/ml *Schinus terebinthifolius* extract.

4. The complex as claimed in claim 2, characterized in that the *Schinus terebinthifolius* extract is obtained by a process comprising the steps of:
    (i) Selecting dry "aroeira" leaves;
    (ii) Grinding the leaves with water;
    (iii) Promoting the aqueous extraction under steam pressure;
    (iv) Filtering the mixture from iii) obtaining a filtrate and supernatant;
    (v) Concentrating the filtrate from iv);
    (vi) Promoting refinement with alcohol;
    (vii) Cooling the product from vi);
    (viii) Evaporating the alcohol; and
    (ix) Drying.

5. The complex as claimed in claim 1, characterized in that the linoleic acid is obtained from passion flower oil.

6. The complex as claimed in claim 5, characterized in that the linoleic acid is obtained by the process comprising the steps of:
    (i) providing passion flower oil;
    (ii) subjecting the passion flower oil to an enzymatic reaction at a temperature from 50° C. to 60° C.;
    (iii) subjecting the product obtained in (ii) to a first molecular distillation at a temperature of 120° C. under vacuum of 0.13 mBar; and
    (iv) subjecting the distillate obtained in (iii) to a second molecular distillation at a temperature of 160° C. under vacuum of 0.002 mBar to obtain a final distillate containing linoleic acid.

7. The complex as claimed in claim 1, characterized in that it comprises from 0.05 mg/ml to 15 mg/ml of ascorbic acid.

8. A cosmetic or pharmaceutical composition characterized in that it comprises a clarifying complex as defined in claim 1 and a physiologically acceptable vehicle.

9. The complex as claimed in claim 1, wherein the complex includes gallic acid present at a concentration from 0.05 mg/ml to 0.075 mg/ml and linoleic acid present at a concentration from 0.025mg/ml to 0.075 mg/ml.

10. The complex as claimed in claim 1, wherein the complex includes a gallic acid to linoleic acid ratio ranging from 1:3 to 3:1.

11. A method of applying a clarifying complex as defined in claim 1, characterized in that it consists of:
    (i) Selecting an area of the body to be depigmentated; and
    (ii) Applying said clarifying complex to said area of the body.

* * * * *